(12) United States Patent
Choi et al.

(10) Patent No.: US 9,284,386 B2
(45) Date of Patent: Mar. 15, 2016

(54) ANSA-METALLOCENE COMPOUND AND METHOD FOR PREPARING SUPPORTED CATALYST USING THE SAME

(71) Applicant: LG CHEM, LTD., Seoul (KR)

(72) Inventors: Yeong-Ah Choi, Daejeon (KR);
Jin-Woo Lee, Daejeon (KR);
Nan-Young Lee, Daejeon (KR);
Churl-Young Park, Daejeon (KR);
Dong-Gil Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/391,474

(22) PCT Filed: May 2, 2013

(86) PCT No.: PCT/KR2013/003807
§ 371 (c)(1),
(2) Date: Oct. 9, 2014

(87) PCT Pub. No.: WO2013/168928
PCT Pub. Date: Nov. 14, 2013

(65) Prior Publication Data
US 2015/0073107 A1 Mar. 12, 2015

(30) Foreign Application Priority Data

May 8, 2012 (KR) .......................... 10-2012-0048850
May 2, 2013 (KR) .......................... 10-2013-0049315

(51) Int. Cl.
| | |
|---|---|
| *C08F 4/6592* | (2006.01) |
| *C08F 4/62* | (2006.01) |
| *C08F 110/06* | (2006.01) |
| *C08F 10/00* | (2006.01) |
| *C08F 4/76* | (2006.01) |
| *B01J 31/12* | (2006.01) |
| *C07F 17/00* | (2006.01) |
| *C08F 4/659* | (2006.01) |

(52) U.S. Cl.
CPC . *C08F 4/76* (2013.01); *B01J 31/12* (2013.01);
*C07F 17/00* (2013.01); *C08F 10/00* (2013.01);
*C08F 110/06* (2013.01); *C08F 4/65908*
(2013.01); *C08F 4/65927* (2013.01)

(58) Field of Classification Search
CPC .. C07F 17/00; C08F 4/65912; C08F 4/65927; C08F 10/00; C08F 10/06; C08F 110/06
See application file for complete search history.

(56) References Cited

U.S. PATENT DOCUMENTS

| | | |
|---|---|---|
| 5,328,969 A | 7/1994 | Winter et al. |
| 5,504,172 A | 4/1996 | Imuta et al. |
| 5,543,373 A | 8/1996 | Winter et al. |
| 5,616,663 A | 4/1997 | Imuta et al. |
| 5,753,785 A | 5/1998 | Reddy et al. |
| 5,776,851 A | 7/1998 | Küber et al. |
| 5,840,644 A | 11/1998 | Küber et al. |
| 5,859,272 A | 1/1999 | Imuta et al. |
| 6,087,292 A | 7/2000 | Winter et al. |
| 6,350,830 B1 | 2/2002 | Goeres et al. |
| 7,094,857 B2 | 8/2006 | Sukhadia et al. |
| 7,232,869 B2 | 6/2007 | Sell et al. |
| 7,468,416 B2 | 12/2008 | Sell et al. |
| 2001/0053833 A1 | 12/2001 | Nakano et al. |
| 2002/0165084 A1 | 11/2002 | Burkhardt et al. |
| 2005/0153830 A1 | 7/2005 | Jensen et al. |
| 2011/0319575 A1 | 12/2011 | Jensen et al. |

FOREIGN PATENT DOCUMENTS

| | | |
|---|---|---|
| EP | 1095944 A1 | 5/2001 |
| EP | 1 996 600 | 9/2011 |
| JP | 2002-504569 | 2/2002 |
| JP | 2003-528167 | 9/2003 |
| JP | 4288658 B2 | 7/2009 |
| KR | 10-2001-0034199 | 4/2001 |
| KR | 10-0297121 | 5/2001 |
| KR | 10-2004-0090773 | 10/2004 |
| KR | 10-2006-0021476 | 3/2006 |
| KR | 10-2007-0104511 | 10/2007 |
| KR | 10-2007-0110249 | 11/2007 |
| KR | 10-2010-0101093 | 9/2010 |
| KR | 10-2011-0013286 | 2/2011 |
| WO | 2011/111980 A2 | 9/2011 |
| WO | 2013/066109 A1 | 5/2013 |

OTHER PUBLICATIONS

Ilya E. Nifant'ev et al., Asymmetric ansa-Zirconocenes Containing a 2-Methyl-4-aryltetrahydroindacene Fragment: Synthesis, Structure, and Catalytic Activity in Propylene Polymerization and Copolymerization. Organometallics, 2011, vol. 30, pp. 5744-5752.

*Primary Examiner* — Caixia Lu
(74) *Attorney, Agent, or Firm* — Dentons US LLP

(57) ABSTRACT

This disclosure relates to an ansa-metallocene compound of a novel structure that can provide various selectivities and activities to polyolefin copolymers, a preparation method thereof, and a method for preparing polyolefins using the ansa-metallocene compound.

17 Claims, No Drawings

ANSA-METALLOCENE COMPOUND AND METHOD FOR PREPARING SUPPORTED CATALYST USING THE SAME

This application is a 35 USC §371 National Stage entry of International Application No. PCT/KR2013/003807, filed May 2, 2013, and claims the benefit of Korean Application Nos. 10-2012-0048850, filed May 8, 2012, and 10-2013-0049315, filed on May 2, 2013, all of which are hereby incorporated by reference in their entirety for all purposes as if fully set forth herein.

TECHNICAL FIELD

The present invention relates to an ansa-metallocene compound and a method for preparing a supported catalyst using the same.

BACKGROUND ART

An ansa-metallocene is an organic metal compound containing two ligands that are linked by a bridge group. The bridge group prevents rotation of the ligands and determines the structure and activity of the metal center.

One potential application of ansa-metallocenes is in polymerization reactions for olefin homopolymers or copolymers. Particularly, ansa-metallocenes based on cyclopentadienyl-fluorenyl ligands have become of great significance in the polymerization of high-molecular weight polyethylenes with controlled microstructures. In addition, ansa-metallocenes containing indenyl ligands have excellent activity and can be used to produce polyolefins with high stereoregularity.

As such, although various studies on ansa-metallocene compounds that have higher activity and yet can control the microstructure of olefin polymers are underway, the results are unsatisfactory.

DISCLOSURE

Technical Problem

It is an object of the present invention to provide an ansa-metallocene compound with a novel structure, and that has excellent activity as a supported catalyst and can simultaneously easily control the microstructure of an olefin polymer.

It is another object of the present invention to provide a method for preparing the ansa-metallocene compound.

It is still another object of the present invention to provide a supported catalyst for olefin polymerization including the ansa-metallocene compound.

It is still another object of the present invention to provide a method for preparing a polyolefin using the supported catalyst.

Technical Solution

The present invention provides an ansa-metallocene compound represented by the following Chemical Formula 1.

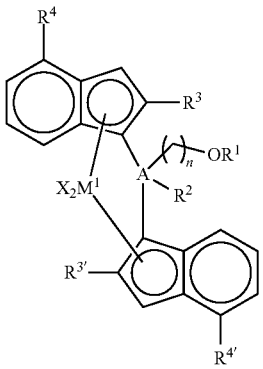

[Chemical Formula 1]

Herein, $M^1$ is a transition metal of Group 3, Group 4, or Group 5 of the Periodic Table, or of an actinide or lanthanide; X's, which may be the same or different, are each a halogen; A is an element of Group 14 of the Periodic Table and functions as a bridge group linking two indenyl groups; $R^1$ is an alkyl having 1 to 20 carbon atoms, an alkenyl having 2 to 20 carbon atoms, an alkylaryl having 7 to 20 carbon atoms, an arylalkyl having 7 to 20 carbon atoms, or an aryl having 6 to 20 carbon atoms; $R^2$ is hydrogen, an alkyl having 1 to 20 carbon atoms, an alkenyl having 2 to 20 carbon atoms, an alkylaryl having 7 to 20 carbon atoms, an arylalkyl having 7 to 20 carbon atoms, or an aryl having 6 to 20 carbon atoms; $R^3$, $R^{3'}$, $R^4$, and $R^{4'}$, which may be the same or different, are independently an alkyl having 1 to 20 carbon atoms, an alkenyl having 2 to 20 carbon atoms, an alkylaryl having 7 to 20 carbon atoms, an arylalkyl having 7 to 20 carbon atoms, or an aryl having 6 to 20 carbon atoms; and n is an integer of 1 to 20.

The present invention also provides a method for preparing the ansa-metallocene compound.

The present invention also provides a supported catalyst for olefin polymerization including the ansa-metallocene compound.

The present invention also provides a method for preparing a polyolefin using the supported catalyst.

Hereinafter, embodiments will be given of the ansa-metallocene compound and a preparation method thereof, a catalyst for olefin polymerization including the same, and a method for preparing a polyolefin using the catalyst. The preferred embodiments of the present invention have been disclosed for illustrative purposes, but are not for limiting the present invention. Thus, those skilled in the art will appreciate that various modifications, additions, and substitutions are possible, without departing from the scope and spirit of the invention as disclosed in the accompanying claims.

As used herein, the term "comprise" or "contain" refer to including a component (or constituent) without limitations, but must not be construed to exclude the addition of other components (or constituents).

During repeated studies on metallocene compounds, the inventors prepared an ansa-metallocene compound containing indenyl groups wherein substituents other than hydrogen are introduced at positions 2 and 4 as ligands, and having a bridge group linking the ligands, which is substituted with an oxygen-donor functioning as a Lewis base, and confirmed that a supported catalyst using the compound as a catalyst precursor can easily prepare a polyolefin having high activity and high molecular weight.

Thus, according to one embodiment of the invention, an ansa-metallocene represented by the following Chemical Formula 1 is provided.

[Chemical Formula 1]

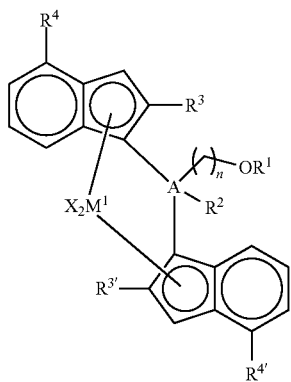

Herein, M¹ is a transition metal of Group 3, Group 4, or Group 5 of the Periodic Table, or of an actinide or lanthanide; X's, which may be the same or different, are each a halogen; A is an element of Group 14 of the Periodic Table and functions as a bridge group linking two indenyl groups; $R^1$ is an alkyl having 1 to 20 carbon atoms, an alkenyl having 2 to 20 carbon atoms, an alkylaryl having 7 to 20 carbon atoms, an arylalkyl having 7 to 20 carbon atoms, or an aryl having 6 to 20 carbon atoms; $R^2$ is hydrogen, an alkyl having 1 to 20 carbon atoms, an alkenyl having 2 to 20 carbon atoms, an alkylaryl having 7 to 20 carbon atoms, an arylalkyl having 7 to 20 carbon atoms, or an aryl having 6 to 20 carbon atoms; $R^3$, $R^{3'}$, $R^4$, and $R^{4'}$, which may be the same or different, are independently an alkyl having 1 to 20 carbon atoms, an alkenyl having 2 to 20 carbon atoms, an alkylaryl having 7 to 20 carbon atoms, an arylalkyl having 7 to 20 carbon atoms, or an aryl having 6 to 20 carbon atoms; and n is an integer of 1 to 20.

Preferably, $R^1$ and $R^2$ are independently an alkyl having 1 to 4 carbon atoms; $R^3$ and $R^{3'}$ are independently an alkyl having 1 to 20 carbon atoms, an alkenyl having 2 to 20 carbon atoms, or an arylalkyl having 7 to 20 carbon atoms; $R^4$ and $R^{4'}$ are independently an aryl having 6 to 20 carbon atoms, or an alkylaryl having 7 to 20 carbon atoms; n is an integer of 1 to 6; and A is silicon (Si).

The ansa-metallocene of Chemical Formula 1 can exert maximal catalytic activity as it contains two indenyl groups as ligands linked by a bridge group which is substituted with an oxygen donor functioning as a Lewis base. Thereby, if the compound of Chemical Formula 1 is used by itself as a catalyst for preparation of a polyolefin or supported on a support and used as a catalyst for polyolefin preparation, a polyolefin having desired properties may be easily prepared.

Meanwhile, according to another embodiment, a method for preparing an ansa-metallocene compound represented by Chemical Formula 1 is provided.

The method for preparing the ansa-metallocene compound represented by Chemical Formula 1 may include reacting a compound represented by the following Chemical Formula a with a compound represented by the following Chemical Formula b to prepare a compound represented by the following Chemical Formula c:

[Chemical Formula a]

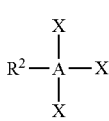

[Chemical Formula b]

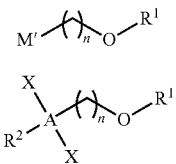

[Chemical Formula c]

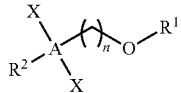

wherein, in Chemical Formulae a, b, and c, A is an element of Group 14 of the Periodic Table; M' is lithium, sodium, potassium, MgCl, MgBr, or MgI; $R^1$ is an alkyl having 1 to 20 carbon atoms, an alkenyl having 2 to 20 carbon atoms, an alkylaryl having 7 to 20 carbon atoms, an arylalkyl having 7 to 20 carbon atoms, or an aryl having 6 to 20 carbon atoms; $R^2$ is hydrogen, an alkyl having 1 to 20 carbon atoms, an alkenyl having 2 to 20 carbon atoms, an alkylaryl having 7 to 20 carbon atoms, an arylalkyl having 7 to 20 carbon atoms, or an aryl having 6 to 20 carbon atoms; X's, which may be the same or different, are each a halogen; and n is an integer of 1 to 20;

reacting a compound represented by the above Chemical Formula c with a compound represented by the following Chemical Formula d to prepare a compound represented by the following Chemical Formula e:

[Chemical Formula d]

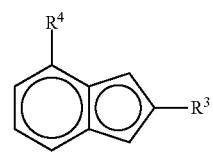

[Chemical Formula e]

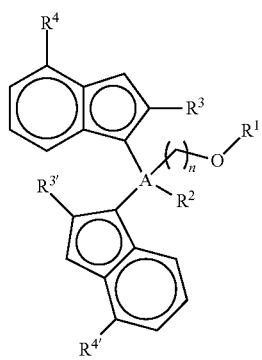

wherein, in Chemical Formulae d and e, A, $R^1$, $R^2$, and n are as defined in Chemical Formula c; $R^3$, $R^{3'}$, $R^4$, and $R^{4'}$, which may be the same or different, are independently an alkyl having 1 to 20 carbon atoms, an alkenyl having 2 to 20 carbon atoms, an alkylaryl having 7 to 20 carbon atoms, an arylalkyl having 7 to 20 carbon atoms, or an aryl having 6 to 20 carbon atoms; and reacting a compound represented by Chemical Formula e with a compound represented by the following Chemical Formula f:

[Chemical Formula f]

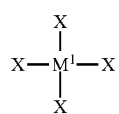

wherein, in Chemical Formula f, $M^1$ is a transition metal of Group 3, Group 4, or Group 5 of the Periodic Table, or of an actinide or lanthanide; and X's, which may be the same or different, are each a halogen.

According to one embodiment of the invention, the step of preparing the compound of Chemical Formula c may include mixing and reacting an organic solution including the compound of Chemical Formula a with an organic solution including the compound of Chemical Formula b, at a temperature of −200° C. to 0° C., preferably −150° C. to 0° C. After separating the organic layer in the mixed solution, a step of vacuum drying the separated organic layer and removing excess reactants may be further conducted.

In addition, the step of preparing the compound of Chemical Formula e may include adding a solution of alkyllithium and the like to the compound of Chemical Formula d, and stirring at 10 to 50° C., preferably 20 to 40° C. Then, the above-prepared compound of Chemical Formula c is added dropwise to the mixed solution, and they are reacted at a temperature of −150° C. to 0° C., preferably −100° C. to 0° C., thereby preparing the compound of Chemical Formula e.

A solution of alkyllithium and the like is then added to the organic solution including the compound of Chemical Formula e, they are reacted at a temperature of −150° C. to 0° C., preferably −100° C. to 0° C., and a compound of Chemical Formula f is added to the reaction product and reacted.

Moreover, other than the above-explained steps, any steps commonly conducted in the art may be further included before or after each step, and the preparation method of the present invention is not limited to the above-explained steps.

Meanwhile, according to another embodiment of the invention, a catalyst for olefin polymerization including the ansa-metallocene compound is provided.

The ansa-metallocene compound according to the present invention may be used as a catalyst for olefin polymerization, as it is or as a catalyst precursor together with a cocatalyst.

The catalyst for olefin polymerization may be a catalyst supported on a support.

As the support, those commonly used in the art may be used without specific limitations, and preferably, at least one selected from the group consisting of silica, silica-alumina, and silica-magnesia may be used. When the catalyst is supported on a silica support, since the silica support and the functional group of the ansa-metallocene compound are chemically bonded, the catalyst is not substantially isolated from the surface in an olefin polymerization process, and thus fouling of polymer particles or a reactor wall surface may not be caused when preparing a polyolefin by slurry or gas phase polymerization.

Further, the polyolefin prepared in the presence of a catalyst including a silica support has excellent apparent density and polymer particle shape, and thus may be suitably used in the conventional slurry or gas phase polymerization process.

Therefore, a support that is dried at a high temperature and has a highly reactive siloxane group on the surface may be preferably used. Specifically, silica dried at a high temperature, silica-alumina, and the like may be used, and they commonly contain an oxide, a carbonate, a sulfate, a nitrate such as $Na_2O$, $K_2CO_3$, $BaSO_4$, $Mg(NO_3)_2$, and the like.

The catalyst for olefin polymerization may further include a cocatalyst consisting of alkylaluminoxane. If the cocatalyst is used, the halogen group (X) bonded to the metal atom ($M^1$) of the metallocene compound may be substituted with an alkyl group, for example, an alkyl having 1 to 20 carbon atoms.

As the cocatalyst, those commonly used in the art may be used without specific limitations, and preferably, at least one cocatalyst selected from the group consisting of silica, silica-alumina, and an organic aluminum compound may be used.

The ansa-metallocene compound catalyst of the present invention is a catalyst that can basically prepare a polyolefin having a high molecular weight, and if hydrogen is added, a polyolefin having a low molecular weight may be effectively prepared even with a small amount of hydrogen, thus broadening the molecular weight range of the final polymer product.

Meanwhile, according to another embodiment of the invention, a method for preparing a polyolefin including polymerizing at least one olefin monomer in the presence of the catalyst for olefin polymerization is provided.

The olefin monomer may be selected from the group consisting of ethylene, propylene, 1-butene, 1-pentene, 1-hexene, 4-methyl-1-pentene, 1-octene, 1-decene, 1-dodecene, 1-tetradecene, 1-hexadecene, 1-octadecene, 1-eicosene, and a combination thereof.

The olefin polymerization may be performed at a temperature of 25 to 500° C. under a pressure of 1 to 100 $kgf/cm^2$ for 1 to 24 hr. The reaction temperature for the polymerization may preferably range from 25 to 200° C. (degrees Celsius), and more preferably from 50 to 100° C. Further, the polymerization pressure may preferably be from 1 to 70 $kgf/cm^2$, and more preferably from 5 to 40 $kgf/cm^2$. The polymerization time may preferably be from 1 to 5 hr.

On the other hand, the polymerization process is designed to adjust the molecular weight of the final polymer product depending on the presence or absence of hydrogen. Particularly, in a hydrogen-free condition, high-molecular weight polyolefins can be prepared. On the other hand, even in the presence of a small amount of hydrogen, low-molecular weight polyolefins can be obtained. In this regard, the hydrogen content used in the polymerization may range from 0.07 L to 4 L under a reactor pressure of 1 atm, or hydrogen may be supplied at a pressure of 1 bar to 40 bar or at a molar ratio to the olefin monomer of 168 ppm to 8000 ppm.

The polyolefin prepared using the ansa-metallocene compound catalyst of the present invention may have a higher molecular weight than that prepared using a conventional metallocene catalyst. Particularly, the polyolefin prepared in the presence of the ansa-metallocene compound catalyst in a hydrogen-free condition may have a weight average molecular weight (Mw) of 200,000 or greater, or from 200,000 to 600,000, preferably 250,000 or greater, and more preferably 300,000 or greater. On the other hand, when a polymerization process is conducted using the ansa-metallocene compound catalyst of the present invention in a hydrogen condition, for example, when 0.37 L of hydrogen is added under the 1 atm pressure of the reactor, the polyolefin may have a weight average molecular weight (Mw) of 90,000 or less, or from 55,000 to 90,000, preferably 85,000 or less, and more preferably 80,000 or less.

As such, low- or high-molecular weight polyolefins can be selectively prepared in the presence of the ansa-metallocene compound catalyst of the present invention, depending on the content of hydrogen.

The polyolefin prepared by the method may have a weight average molecular weight/number average molecular weight distribution (Mw/Mn) of 3.3 or less, or 1 to 3.3, preferably 1.5 to 3.2, and more preferably 2 to 3.

The catalyst for olefin polymerization including the ansa-metallocene compound of the present invention may have catalytic activity of 20 kg/mmol·hr or more, or 20 to 160 kg/mmol·hr, preferably 50 kg/mmol·hr or more, more preferably 70 kg/mmol·hr or more, as calculated by the ratio of the weight (kg) of the produced polymer per mmol of the used catalyst per unit time (hr). Moreover, when calculated as the weight (kg) of the polymer produced per weight (g) of the catalyst per unit time (hr), the catalyst may exhibit catalytic activity of 1.0 kg/gCat·hr or more, 1.0 to 10 kg/gCat·hr, preferably 2.0 kg/gCat·hr or more, and more preferably 3.0 kg/gCat·hr or more.

The polyolefin may have stereoregularity (XI) of 90% or higher, preferably 92% or higher, and more preferably 95% or higher. In this regard, the stereoregularity (XI) is calculated according to the following Equation 1.

$$\text{Stereoregularity}(XI) = 100 - Xs \quad \text{[Equation 1]}$$

$$Xs = \left(\frac{Vbo}{Vb1} \times (W2 - W1) - \frac{Vbo}{Vb2} \times B\right) \Big/ Wo \times 100$$

Herein,

Xs=soluble fraction of a polymer in o-xylene (wt %),

Vb0=initial volume of o-xylene (mL),

Vb1=volume of sample taken from the polymer dissolved in o-xylene (mL),

Vb2=volume of o-xylene sample used in the blank test (mL),

W2=weight of the polymer left on the aluminum pan after evaporation of o-xylene plus weight of the aluminum pan itself (g), W1=weight of the aluminum pan (g), W0=initial weight of the polymer (g), and B=average weight of the residue on the aluminum pan in the blank test (g).

The polyolefin prepared by bulk polymerization according to the present invention may remarkably improve the melting point (Tm) as well as stereoregularity (XI). The melting point of the polyolefin may be 140° C. or more, or 140 to 180° C., preferably 143° C. or more, and more preferably 145° C. or more.

In the present invention, details other than described above may be adjusted as necessary, and are not specifically limited.

Advantageous Effects

The ansa-metallocene compound according to the present invention has excellent catalytic activity, and if a polyolefin is prepared using the same as a catalyst or as a catalyst precursor, the microstructure of the polymer may be easily controlled, thus easily preparing polyolefins having desired properties.

MODE FOR INVENTION

A better understanding of the present invention may be obtained through the following examples which are set forth to illustrate, but are not to be construed as limiting, the present invention.

Example 1

An ansa-metallocene compound of Chemical Formula 2 and a supported catalyst for olefin polymerization including the same were prepared under the conditions described in the following Table 1.

[Chemical Formula 2]

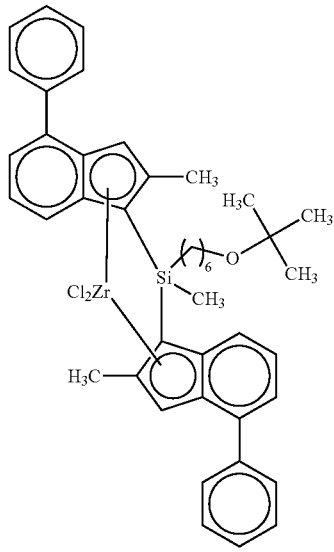

Synthesis of Metallocene

Step 1: Synthesis of (6-t-butoxyhexyl)dichloromethylsilane

To 100 mL of a trichloromethylsilane solution (about 0.21 mol, hexane) was slowly added dropwise 100 mL of a t-butoxyhexyl magnesium chloride solution (about 0.14 mol, ether) at −100° C. for 3 hr, followed by stirring at room temperature for 3 hr.

After being withdrawn from the solution mixture, a transplant organic layer thus formed was dried in a vacuum, and the removal of excess trichloromethylsilane afforded (6-t-butoxyhexyl)dichloromethylsilane as a transparent liquid (yield 84%).

$^1$H NMR (500 MHz, CDCl$_3$, 7.24 ppm): 0.76 (3H, s), 1.11 (2H, t), 1.18 (9H, s), 1.32~1.55 (8H, m), 3.33 (2H, t)

Step 2: Synthesis of (6-t-butoxyhexyl)(methyl)-bis (2-methyl-4-phenylindenyl)silane To 77 mL of a 2-methyl-4-phenylindene toluene/THF=10/1 solution (34.9 mmol), 15.4 mL of an n-butyllithium solution (2.5 M, hexane) was slowly added dropwise at 0° C., followed by stirring the reaction mixture at 80° C. for 1 hr and then overnight at room temperature. Thereafter, 5 g of (6-t-butoxyhexyl)dichloromethylsilane prepared in step 1 was slowly added dropwise at −78° C. to this reaction mixture, and the resulting mixture was stirred for 10 min and then for 80° C. for 1 hr. After washing with water, the organic layer thus formed was purified by silica column chromatography, and dried in a vacuum to afford the title compound as a yellow oil with a yield of 78% (racemic:meso=1:1).

$^1$H NMR (500 MHz, CDCl$_3$, 7.24 ppm): 0.10 (3H, s), 0.98 (2H, t), 1.25 (9H, s), 1.36~1.50 (8H, m), 1.62 (8H, m), 2.26 (6H, s), 3.34 (2H, t), 3.81 (2H, s), 6.87 (2H, s), 7.25 (2H, t), 7.35 (2H, t), 7.45 (4H, d), 7.53 (4H, t), 7.61 (4H, d)

Step 3: Synthesis of [(6-t-butoxyhexylmethylsilane-diyl)-bis(2-methyl-4-phenylindenyl)]zirconium dichloride To 50 mL of the above prepared (6-t-butoxyhexyl)(methyl)bis(2-methyl-4-phenyl)indenylsilane ether/hexane=1/1 (3.37 mmol), 3.0 mL of n-butyllithium (2.5 M in hexane) was added dropwise at −78° C., followed by stirring at room temperature for about 2 hours and then drying in a vacuum. Subsequently, the resulting salt was washed with hexane, filtered, and dried in a vacuum to give a yellowish solid. The ligand salt prepared in a glove box and bis(N,N′-diphenyl-1,3-propanediamido) dichlorozirconium-bis(tetrahydrofuran) [Zr($C_5H_6NCH_2CH_2CH_2NC_5H_6$)$Cl_2$($C_4H_8O$)$_2$] were weighed and placed in a Schlenk flask to which ether was then slowly added dropwise at −78° C. before stirring at room temperature for one day. Subsequently, the red reaction solution was separated by filtration, and then 4 equivalents of a HCl ether solution (1M) were slowly added dropwise at −78° C., followed by stirring at room temperature for 3 hours. Filtration and then vacuum drying afforded the ansa-metallocene compound as an orange solid with an 85% yield (racemic:meso=10:1).

$^1$H NMR (500 MHz, $C_6D_6$, 7.24 ppm): 1.19 (9H, s), 1.32 (3H, s), 1.48~1.86 (10H, m), 2.25 (6H, s), 3.37 (2H, t), 6.95 (2H, s), 7.13 (2H, t), 7.36 (2H, d), 7.43 (6H, t), 7.62 (4H, d), 7.67 (2H, d)

Preparation of Supported Catalyst

To a Schlenk flask where silica weighing 3 g was placed, 52 mmol of methylaluminoxane (MAO) was added, followed by reaction at 90° C. for 24 hr. After precipitation, the supernatant was removed and the precipitate thus formed was washed twice with toluene. 240 μmol of the above synthesized ansa-metallocene compound was dissolved in toluene, and then reacted at 40° C. for 5 hr. After completion of the reaction and precipitation, the supernatant was removed and the precipitate thus formed was washed twice with toluene and then hexane, and then vacuum dried to yield 5 g of a silica-supported metallocene catalyst in the form of solid particles.

Comparative Example 1

An ansa-metallocene compound of Chemical Formula 3 and a catalyst for olefin polymerization including the same were prepared under the conditions described in the following Table 1.

[Chemical Formula 3]

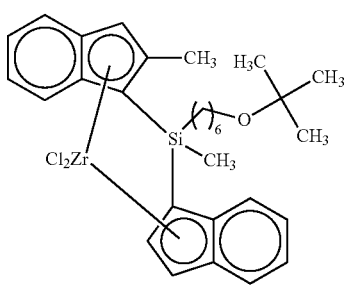

Preparation of Metallocene Compound

Step 1: Synthesis of (6-t-butoxyhexyl)dichloromethylsilane (6-t-butoxyhexyl)dichloromethylsilane was prepared by the same method as Example 1.

Step 2: Synthesis of 6-t-butoxyhexyl-bisindenylmethylsilane

To 50 mL of an indene solution (77.55 mmol in ether), 27.9 mL of an n-butyllithium solution (2.5 M in hexane) was slowly added dropwise at 0° C., followed by stirring the reaction mixture at room temperature for about 2 hr. Thereafter, to this reaction mixture, 9.96 g of (6-t-butoxyhexyl)dichloromethylsilane prepared in step 1 was slowly added dropwise at −78° C., and the resulting mixture was stirred for 10 minutes and then at room temperature for about 3 hr. Subsequently, the reaction product was filtered and vacuum dried to yield 6-t-butoxyhexyl-bisindenylmethylsilane as a sticky oil (yield of 75%).

$^1$H NMR (500 MHz, $CDCl_3$, 7.26 ppm): 1.35 (2H, m), 1.55 (2H, m), 1.62 (12H, m), 1.90~1.67 (6H, m), 3.76 (3H, m), 4.04 (2H, m), 6.82 (1H, t), 7.04 (1H, d), 7.34 (1H, d), 7.38 (1H, t), 7.63 (2H, m), 7.70 (2H, m), 7.83 (1H, d), 7.93 (3H, m)

Step 3: Synthesis of [(6-t-butoxyhexylmethylsilane-diyl)-bis(indenyl)]zirconium dichloride To 50 mL of the above-prepared (6-t-butoxyhexyl)-bis(indenyl)methylsilane solution (29 mmol, ether), 26 mL of an n-butyllithium solution (2.5 M in hexane) was slowly added dropwise at −78° C., followed by stirring at room temperature and then drying in a vacuum. Subsequently, the resulting salt was washed with hexane, filtered, and vacuum dried to give a white solid. To this, toluene and dimethoxyethane were added and dissolved, a $ZrCl_4$ toluene slurry was added at −78° C., and the mixture was stirred at room temperature for about 3 hr. Subsequently, the reaction product was vacuum dried and hexane was added, and then filtration at a low temperature afforded [(6-t-butoxyhexylmethylsilane-diyl)-bis(indenyl)]zirconium dichloride as an orange solid.

$^1$H NMR (500 MHz, $C_6D_6$, 7.26 ppm): 1.17 (12H, m), 1.70~1.20 (10H, m), 3.32 (2H, m), 5.86 (2H, dd), 6.89 (1H, m), 7.01 (2H, m), 7.17 (2H, m), 7.29 (2H, d), 7.32 (2H, m), 7.40 (2H, d)

Preparation of Supported Catalyst

A silica-supported catalyst was prepared by the same method as Example 1, except using the above synthesized ansa-metallocene compound [(6-t-butoxyhexylmethylsilane-diyl)-bis(indenyl)]zirconium dichloride.

Comparative Example 2

An ansa-metallocene compound of Chemical Formula 4 and a catalyst for olefin polymerization including the same were prepared under the conditions described in the following Table 2.

[Chemical Formula 4]

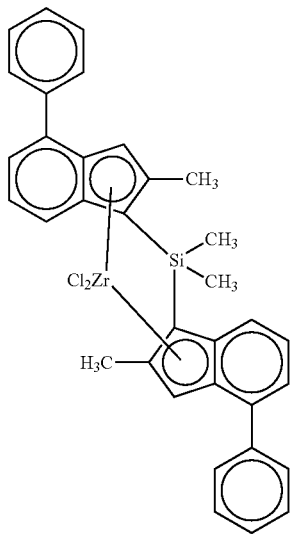

Preparation of Metallocene Compound

Step 1: Synthesis of dimethylbis(2-methyl-4-phenylindenyl)silane

To 77 mL of a 2-methyl-4-phenylindene toluene/THF=10/1 solution (49.5 mmol), 21.8 mL of an n-butyllithium solution (2.5 M, hexane solvent) was slowly added dropwise at 0° C., followed by stirring at 80° C. for 1 hr, and then at room temperature for one day. Thereafter, 2.98 mL of dichloromethylsilane was slowly added dropwise at a temperature equal to or less than 0° C., the reaction mixture was stirred at about 10 minutes, and stirred for 1 hr while the temperature was elevated to 80° C. Subsequently, water was added to separate an organic layer, and then silica column purification and vacuum drying afforded a sticky yellow oil with a yield of 61% (racemic:meso=1:1).

$^1$H NMR (500 MHz, CDCl$_3$, 7.24 ppm): 0.02 (6H, s), 2.37 (6H, s), 4.00 (2H, s), 6.87 (2H, t), 7.38 (2H, t), 7.45 (2H, t), 7.57 (4H, d), 7.65 (4H, t), 7.75 (4H, d)

Step 2: Synthesis of [dimethylsilanediylbis(2-methyl-4-phenylindenyl)]zirconium dichloride To 240 mL of a dimethylbis(2-methyl-4-phenylindenyl)silane ether/hexane=1/1 solution (12.4 mmol), 10.9 mL of an n-butyllithium solution (2.5 M in hexane) was slowly added dropwise at −78° C. Thereafter, the reaction mixture was stirred at room temperature for one day, and then filtered and vacuum dried to obtain a light yellow solid. The ligand salt synthesized in a glove box and bis(N,N'-diphenyl-1,3-propanediamido(dichlorozirconiumbis)(tetrahydrofuran) were weighed in a Schlenk flask, then ether was slowly added dropwise at −78° C., and the reaction mixture was stirred for one day. The resulting red solution was separated by filtration, vacuum dried, and a toluene/ether=1/2 solution was added to yield a clean red solution. 1.5~2 equivalents of a HCl ether solution (1M) was slowly added dropwise at −78° C., followed by stirring at room temperature for 3 hr. Subsequently, the reaction solution was filtered and vacuum dried to obtain an orange solid catalyst with a yield of 70% (racemic only).

$^1$H NMR (500 MHz, C$_6$D$_6$, 7.24 ppm): 1.32 (6H, s), 2.24 (6H, s), 6.93 (2H, s), 7.10 (2H, t), 7.32 (2H, t), 7.36 (2H, d), 7.43 (4H, t), 7.60 (4H, d), 7.64 (2H, d)

Preparation of Supported Catalyst

A silica-supported metallocene catalyst was prepared by the same method as Example 1, using the above synthesized metallocene compound, dimethylsilanediylbis(2-methyl-4-phenylindenyl)]zirconium dichloride.

Comparative Example 3

An ansa-metallocene compound of Chemical Formula 5 and a catalyst for olefin polymerization including the same were prepared as follows, under the conditions described in the following Table 1.

[Chemical Formula 5]

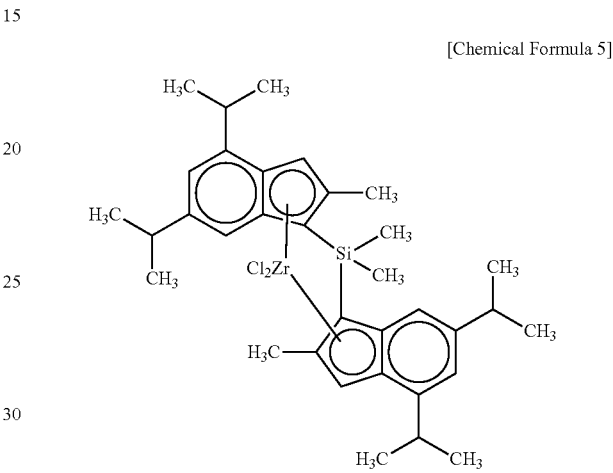

Preparation of Metallocene Compound

Step 1: Synthesis of dimethylbis(2-methyl-4,6-diisopropylindenyl) silane

To 10 mL of a 2-methyl-4,6-isopropylidene solution (3.45 mmol in ether), 7.83 mL of an n-butyllithium solution (2.5 M in hexane) was slowly added dropwise at 0° C., followed by stirring the mixed solution at room temperature for about 3 hr. Then, 0.2 mL of dichloromethylsilane was slowly added dropwise at a temperature less than or equal to 0° C., stirred for about 10 minutes, and then the temperature was elevated to room temperature and the mixed solution was stirred for 3 hr. Subsequently, the reaction product was filtered and vacuum dried to yield dimethylbis(2-methyl-4,6-diisopropylindenyl)silane.

$^1$H NMR (500 MHz, CDCl$_3$, 7.24 ppm): 0.39 (6H, s), 1.30~1.23 (24H, m), 2.25 (6H, m), 2.91 (2H, q), 3.18 (2H, q), 3.53 (2H, s), 6.71 (2H, s), 6.95 (2H, s), 7.14 (2H, s)

Step 2: Synthesis of [dimethylsilanediylbis(2-methyl-4,6-diisopropylindenyl)]zirconium dichloride To 10 mL of a dimethylbis(2-methyl-4,6-diisopropylindenyl)silane solution (2.55 mmol in ether) 2.3 mL of an n-butyllithium solution (2.5 M in hexane) was slowly added dropwise at 0° C., followed by stirring at room temperature for about 4 hr and then vacuum drying. The salt was then washed with hexane, filtered, and vacuum dried to obtain a white solid. To this, toluene and dimethoxyethane were added and dissolved, a ZrCl$_4$ toluene slurry was added at −78° C., and the mixture was stirred at room temperature for about 3 h. Subsequently, the mixture was vacuum dried, hexane was added, and then the mixture was filtered at a low temperature to yield [dimethylsilanediylbis(2-methyl-4,6-diisopropylindenyl)]zirconium dichloride (racemic:meso=1:1).

$^1$H NMR (500 MHz, C$_6$D$_6$, 7.24 ppm): 1.19~1.34 (30H, m), 2.22 (6H, s), 2.84 (2H, q), 3.03 (2H, q), 6.79 (2H, s), 7.04 (2H, q), 7.27 (2H, s)

Preparation of Supported Catalyst

A silica-supported metallocene catalyst was prepared by the same method as Example 1, except using the above synthesized ansa-metallocene compound [dimethylsilanediylbis(2-methyl-4,6-diisopropylindenyl)]zirconium dichloride.

Comparative Example 4

An ansa-metallocene compound of Chemical Formula 6 and a catalyst for olefin polymerization including the same were prepared as follows, under the conditions described in the following Table 1.

[Chemical Formula 6]

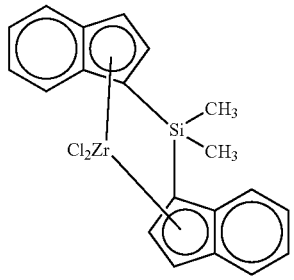

Preparation of Metallocene Compound

Synthesis of (dimethylsilanediyl-bisindenyl) zirconium dichloride

To a solution containing 44 mL of indene and 150 mL of tetrahydrofuran (THF), 215 mL of a methyllithium solution (1.4 M in THF) was slowly added dropwise at 0° C., followed by stirring at room temperature for about 2 h, and then vacuum drying. Subsequently, 225 mL of a methyllithium solution (1.4 M in THF) was slowly added dropwise at 0° C., and the mixture was reacted while stirring at room temperature for about 1 h. Meanwhile, in 200 cc of −80° C. THF, 40 g of zirconium tetrachloride was introduced, and then the temperature was elevated to 25° C. To this, the above mixed and reacted indene solution was slowly introduced into the zirconium halide solution, and the mixture was reacted while stirring at 25° C. for 1 hr. The mixture was dried for 24 hr to obtain an oily substance, which was filtered to obtain (dimethylsilanediyl-bisindenyl)zirconium dichloride as a yellow solid.

$^1$H NMR (500 MHz, C$_6$D$_6$, 7.26 ppm): 0.54 (6H, s), 5.774 (2H, d), 6.80 (2H, d), 6.86 (2H, t), 7.14 (2H, t), 7.22 (2H, d), 7.33 (2H, d)

Preparation of Supported Catalyst

A silica-supported metallocene catalyst was prepared by the same method as Example 1, except using the above synthesized ansa-metallocene compound (dimethylsilanediyl-bisindenyl) zirconium dichloride.

TABLE 1

| | Example 1 | Comparative Example 1 | Comparative Example 2 | Comparative Example 3 | Comparative Example 4 |
|---|---|---|---|---|---|
| R$^1$ | t-Bu | t-Bu | —* | —* | —* |
| N | 6 | 6 | —* | —* | —* |
| R$^2$ | CH$_3$ | CH$_3$ | CH$_3$ | CH$_3$ | CH$_3$ |
| R$^3$, R$^{3'}$ | CH$_3$ | H | CH$_3$ | CH$_3$ | H |
| R$^4$, R$^{4'}$ | Ph | H | Ph | iso-Propyl (4,6-position isopropyhl)** | H |
| Kind of cocatalyst compounds | MAO | MAO | MAO | MAO | MAO |
| Reaction temperature (° C.) | 40 | 40 | 40 | 40 | 40 |
| Reaction time (hr) | 5 | 5 | 5 | 5 | 5 |
| Kind of support | silica | silica | silica | silica | silica |
| Catalyst form | powder | powder | powder | powder | powder |

*In Comparative Examples 2, 3, and 4, the bridge group Si is substituted with —(CH$_3$)$_2$
**In Comparative Example 3, the 2-position of the indenyl group is substituted with a methyl group, and the 4,6-positions are substituted with isopropyl groups.

Preparation Examples 1~2 and Comparative Preparation Examples 1~4

Polypropylene polymers were prepared as follows, respectively using the metallocene catalyst prepared in Example 1 and Comparative Examples 1~4.

Propylene Polymerization

First, a 2 L stainless reactor was vacuum dried at 65° C. and cooled, 1.5 mmol of triethylaluminum was introduced therein at room temperature, and 0.37 L of hydrogen and 1.5 L of propylene were sequentially introduced. Thereafter, the mixture was stirred for 10 minutes, and then each metallocene catalyst prepared in Example 1 and Comparative Examples 1~3 was introduced in the reactor under nitrogen pressure, corresponding to the catalyst amounts as recited in Table 2, below. At this time, hydrogen gas was introduced together with the metallocene catalyst. Subsequently, the temperature of the reactor was slowly elevated to 70° C. at which polymerization was progressed for 1 hr. After completion of the reaction, unreacted propylene monomers were vented.

Measurement was made of contents and activities of the catalysts, and properties of the produced polymers, and data are summarized in Table 2, below.

<Method of Measuring Polymer Properties>

(1) Catalytic activity: the ratio of the weight of the produced polymer (kg PP) per amount of the catalyst used (mmol and g) per unit time (hr).

(2) Melting point of polymer (Tm): melting points of polymers were measured using a differential scanning calorimeter (DSC2920, TA Instruments). Briefly, the temperature of a polymer was increased to 220° C. and maintained for 5 min thereat, and then decreased to 20° C. from which the temperature was again elevated. In this regard, the temperature was increased and decreased at a constant rate of 10° C./min.

(3) Crystallization temperature of polymer (Tc): Tc was determined from a curve drawn during the temperature decrease under the same conditions as for the melting point using DSC.

(4) Stereoregularity of polymer (XI): the % weight percent of the insoluble fraction of the polymer after it was dissolved for 1 hr in boiling ortho-xylene.

Briefly, 200 mL of o-xylene in a flask was filtered through 200 mm No. 4 filter paper. Separately, an aluminum pan was dried in an oven for 30 min at 150° C., cooled in a desiccator, and weighed. Then, 100 mL of the filtered o-xylene was pipetted to the aluminum pan which was then heated to 145~150° C. thereby completely evaporating the o-xylene. Subsequently, the aluminum pan was dried in a vacuum at 100±5° C. for 1 hr under a pressure of 13.3 kPa. Then, the aluminum pan was cooled in the desiccator. This procedure was repeated twice to complete a blank test for o-xylene alone, within a weight error of 0.0002 g.

Next, the polymers produced by the above propylene polymerization process were dried (70° C., 13.3 kPa, 60 min, in a vacuum), and 2±0.0001 g of a sample of the polymers cooled in the desiccator was placed in a 500 mL flask to which 200 mL of o-xylene was then introduced. While the flask was continuously supplied with nitrogen and cooling water, the o-xylene was refluxed for 1 hr at an elevated temperature. Then, the flask was cooled for 5 min in the air to less than 100° C., shaken, and put in a water bath (25±0.5° C.) for 30 min to precipitate the insoluble fraction. The resulting solution having precipitates was filtered through 200 mm No. 4 extraction paper repeatedly until the solution became clear. The filtrate was dried at 150° C. for 30 min, and cooled in the desiccator. Of the clear filtrate, 100 mL was placed on the aluminum pan the weight of which was previously measured. The o-xylene was evaporated by heating the aluminum pan at 145~150° C. After completion of the evaporation, the aluminum pan was dried in a vacuum at 70±5° C. under a pressure of 13.3 kPa for 1 hr and cooled in a desiccator. This procedure was repeated twice to measure the weight of the soluble fraction within a weight error of 0.0002 g.

Weight % percent of the soluble fraction (Xs) of the polymer in o-xylene was calculated according to the following Equation 1, and used to obtain weight % percent of the insoluble fraction of the polymer as stereoregularity (XI).

Equation 1

Stereoregularity (XI)=100-Xs $$\text{Stereoregularity}(XI) = 100 - Xs \quad \text{[Equation 1]}$$

$$Xs = \left(\frac{Vbo}{Vb1} \times (W2 - W1) - \frac{Vbo}{Vb2} \times B\right) \bigg/ Wo \times 100$$

Herein,
Xs=soluble fraction of a polymer in o-xylene (wt %),
Vb0=initial volume of o-xylene (mL),
Vb1=volume of sample taken from the polymer dissolved in o-xylene (mL),
Vb2=volume of o-xylene sample used in the blank test (mL),
W2=weight of the polymer left on the aluminum pan after evaporation of o-xylene plus weight of the aluminum pan itself (g),
W1=weight of the aluminum pan (g),
W0=initial weight of polymer (g), and
B=average weight of the residue on the aluminum pan in the blank test (g).

(5) Molecular weight distribution (PDI, polydispersity index) and weight average molecular weight (Mw) of polymer: The weight average molecular weight (Mw) and the number average molecular weight (Mn) of the polymer were measured using gel permeation chromatography (GPC, Waters), and the molecular weight distribution (PDI) was calculated by dividing the weight average molecular weight by the number average molecular weight. For this, the molecular weights were measured at 160° C. in trichlorobenzene in normalization to polystyrene.

Polymerization process conditions in Preparation Examples 1~2 and Comparative Preparation Examples 1~4 using the metallocene catalyst prepared in Example 1 and Comparative Examples 1~4, and the properties of the prepared polypropylenes, are summarized in Table 2, below.

TABLE 2

| Kind of catalysts | Preparation Example 1 Example 1 | Preparation Example 2 Example 1 | Comparative Preparation Example 1 Comparative Example 1 | Comparative Preparation Example 2 Comparative Example 2 | Comparative Preparation Example 3 Comparative Example 3 | Comparative Preparation Example 4 Comparative Example 4 |
|---|---|---|---|---|---|---|
| Liquid propylene (L) | 1.5 | 1.5 | 1.5 | 1.5 | 1.5 | 1.5 |
| Catalyst amount (μmol) | 2.07 | 1.96 | 17 | 5.50 | 5.50 | 5.50 |
| Polymerization method | Bulk polymerization | Bulk polymerization | Bulk polymerization | Bulk polymerization | Bulk polymerization | Bulk polymerization |
| Polymerization temperature (° C.) | 70 | 70 | 70 | 70 | 70 | 70 |
| Hydrogen (bar) | — | 5 | — | — | — | — |
| Activity (kg/mmol · hr) | 80.9 | 138.5 | 6.0 | 14.6 | — | 14.3 |
| Activity (kg/gCat · hr) | 3.05 | 5.21 | 0.30 | 0.55 | — | 0.54 |
| Tm (° C.) | 148.4 | 150.4 | 138.7 | 152.7 | — | 135.2 |
| Tc (° C.) | 107.2 | 109.6 | 110.7 | 112.1 | — | 107.0 |
| Xs (%) | 1.78 | 1.82 | 10.2 | 0.61 | — | 3.33 |
| XI (%) | 98.22 | 98.18 | 89.8 | 99.39 | — | 96.67 |
| Mw | 381,000 | 76,500 | 34,200 | 608,000 | — | 24,800 |
| MWD | 2.19 | 2.57 | 3.41 | 1.98 | — | 2.10 |

As shown in Table 2, in Preparation Examples 1~2 wherein metallocene compounds having indenyl groups and specific substituents at the bridge groups are used as supported catalysts, high activity and molecular weight increasing effect can be achieved when preparing a polyolefin. Particularly, in Preparation Examples 1~2, catalytic activities are excellent at 80.9~138.5 kg/mmol·hr and 3.05~5.21 kg/gCat·hr, and the produced polymers have much improved stereoregularity (XI) of 98.18%~98.22%. In addition, polypropylene polymers produced by Preparation Examples 1~2 have excellent molecular weight distribution (MWD: Mw/Mn) of 2.19~2.57.

Meanwhile, in Preparation Examples 1 and 2, the activity is further increased by the addition of hydrogen when polymerizing, and a high flow polymer may be effectively prepared even by adding a small amount of hydrogen. Particularly, in the case of Preparation Example 1, polypropylene having a high molecular weight of 381,000 may be prepared with high activity by conducting a polymerization process without adding hydrogen. Further, in the case of Preparation Example 2, polypropylene having low molecular weight of 76,500 may also be prepared with high activity by adding a small amount of hydrogen in the polymerization process. In addition, the polypropylene polymers produced by Preparation Examples 1~2 have a significantly improved melting point (Tm) of 148.4 to 150.4° C.

To the contrary, in Comparative Preparation Examples 1~2 wherein metallocene compounds without specific substituents are used as catalysts, the catalytic activity and the stereoregularity of produced polyolefins and the like are remarkably decreased. Particularly, in the case of Comparative Preparation Example 1, when a polymerization process is conducted using a metallocene compound that does not contain a specific substituent at the indenyl group as a catalyst, catalytic activity is remarkably decreased at 6.05 kg/mmol·hr and 0.30 kg/gCat·hr, and the stereoregularity (XI) of the produced polymer is not good at 89.8%.

Further, in the case of Comparative Preparation Example 2 wherein a metallocene compound that does not contain a specific substituent at the bridge group while the bridge group being substituted with a methyl group is used as a catalyst, catalytic activity is not good at 14.6 kg/mmol·hr and 0.55 kg/gCat·hr. It can be seen that in Comparative Preparation Example 2, support efficiency is lowered and activity is decreased because an oxygen-donor functional group is not included in the bridge group. Furthermore, in the case of Comparative Preparation Example 3 wherein a metallocene compound having different substituents of the indenyl groups and a different substituent of the bridge group is used as a catalyst, polymerization does not occur at all, and thus it can be seen that the [dimethylsilanediylbis(2-methyl-4,6-diisopropylindenyl)]zirconium dichloride catalyst precursor has low activity, and that the formation of a supported catalyst is not achieved.

Also, in the case of Comparative Preparation Example 4 wherein the existing metallocene compound that does not contain a specific substituent at the indenyl group while the bridge group is substituted only with methyl groups, the catalytic activity is not good at 14.3 kg/mmol·hr and 0.54 kg/gCat·hr. In addition, it can be seen that in the case of Comparative Preparation Example 4, a very low molecular weight is exhibited although the same conditions as Preparation Example 1 are applied, and a high molecular polypropylene polymer cannot be produced. Particularly, in the case of Comparative Preparation Example 4, catalytic components are discharged from the supported catalyst when polymerizing, thus generating fouling in the reactor.

Furthermore, it can be seen that the polypropylene polymers produced by Comparative Preparation Examples 1 and 4 have remarkably decreased melting points (Tm) of 138.7° C. and 135.2° C., respectively.

The invention claimed is:

1. An ansa-metallocene compound represented by the following Chemical Formula 1:

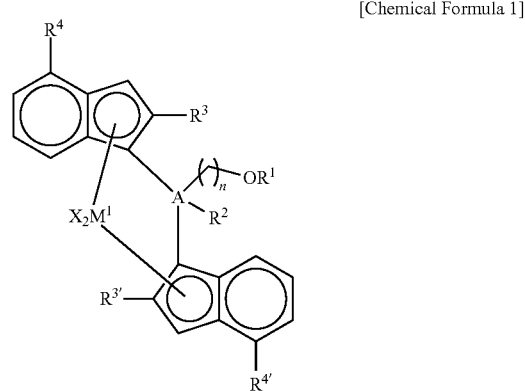

[Chemical Formula 1]

wherein $M^1$ is a transition metal of Group 3, Group 4, or Group 5 of the Periodic Table, or of an actinide or lanthanide; X's, which are optionally the same or different, are each a halogen; $R^1$ and $R^2$ are independently an alkyl having 1 to 4 carbon atoms; $R^3$ and $R^{3'}$, which are optionally the same or different, are independently an alkyl having 1 to 20 carbon atoms, an alkenyl having 2 to 20 carbon atoms, or an arylalkyl having 7 to 20 carbon atoms; $R^4$ and $R^{4'}$, which are optionally the same or different, are independently an aryl having 6 to 20 carbon atoms, or an alkylaryl having 7 to 20 carbon atoms; n is an integer of 1 to 6; and A is silicon (Si).

2. The ansa-metallocene compound according to claim 1, wherein $R^3$ and $R^{3'}$ are independently methyl; $R^4$ and $R^{4'}$ are independently phenyl; and n is 6.

3. A method for preparing the ansa-metallocene compound represented by Chemical Formula 1 of claim 1, comprising reacting a compound represented by the following Chemical Formula a with a compound represented by the following Chemical Formula b to prepare a compound of the following Chemical Formula c:

[Chemical Formula a]

[Chemical Formula b]

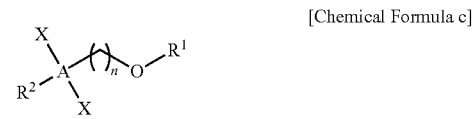

[Chemical Formula c]

wherein, in Chemical Formulae a, b, and c, A is silicon (Si); M' is lithium, sodium, potassium, MgCl, MgBr, or MgI; $R^1$ and $R^2$ are independently an alkyl having 1 to 4 carbon atoms; X's, which are optionally the same or different, are each a halogen; and n is an integer of 1 to 6, reacting the compound of Chemical Formula c with a compound represented by the following Chemical Formula d to prepare a compound of the following Chemical Formula e:

[Chemical Formula d]

[Chemical Formula e]

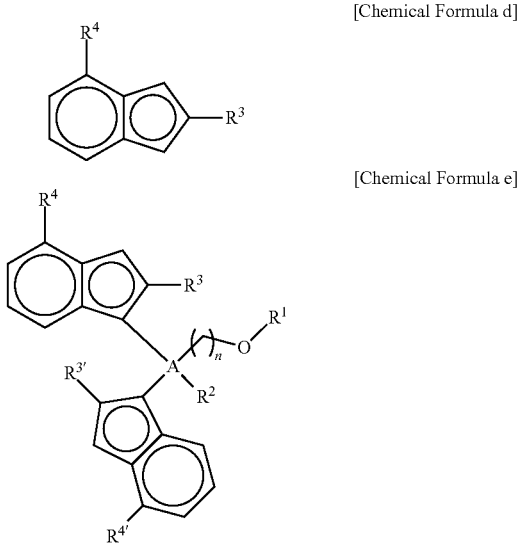

wherein, in Chemical Formulae d and e, A, $R^1$, $R^2$, and n are as defined in Chemical Formula c; $R^3$ and $R^{3'}$, which are optionally the same or different, are independently an alkyl having 1 to 20 carbon atoms, an alkenyl having 2 to 20 carbon atoms, or an arylalkyl having 7 to 20 carbon atoms; $R^4$ and $R^{4'}$, which are optionally the same or different, are independently an aryl having 6 to 20 carbon atoms, or an alkylaryl having 7 to 20 carbon atoms, and reacting a compound represented by the above Chemical Formula e with a compound represented by the following Chemical Formula f:

[Chemical Formula f]

wherein, in Chemical Formula f, $M^1$ is a transition metal of Group 3, Group 4, or Group 5 of the Periodic Table, or is an actinide or lanthanide; and X's, which are optionally the same or different, are each a halogen.

4. A catalyst for olefin polymerization comprising the ansa-metallocene compound according to claim 1.

5. The catalyst for olefin polymerization according to claim 4, wherein the ansa-metallocene compound is supported on a support selected from the group consisting of silica, silica-alumina, silica-magnesia, and combinations thereof.

6. A method for preparing a polyolefin comprising polymerizing at least one olefin monomer in the presence of the catalyst according to claim 4.

7. The method according to claim 6, wherein the polymerization is carried out at a temperature of 25 to 500° C. under a pressure of 1 to 100 kgf/cm² for 1 to 24 hr.

8. The method according to claim 6, wherein the olefin monomers are selected from the group consisting of ethylene, propylene, 1-butene, 1-pentene, 1-hexene, 4-methyl-1-pentene, 1-octene, 1-decene, 1-dodecene, 1-tetradecene, 1-hexadecene, 1-octadecene, 1-eicosene, and a combination thereof.

9. The method according to claim 6, wherein the activity of the catalyst is 20 kg/mmol·hr or more, as calculated by the ratio of weight (kg) of the produced polymer per mmol of the used catalyst per unit time (hr), after propylene polymerization is carried out at a temperature of 25 to 500° C. under a pressure of 1 to 100 kgf/cm² for 1 to 24 hr by using triethylaluminum, hydrogen, propylene, and the catalyst.

10. The method according to claim 6, wherein the activity of the catalyst is 1.0 kg/gCat·hr or more, as calculated by the ratio of the weight (kg) of the produced polymer per weight (g) of the used catalyst per unit time (hr), after propylene polymerization is carried out at a temperature of 25 to 500° C. under a pressure of 1 to 100 kgf/cm² for 1 to 24 hr by using triethylaluminum, hydrogen, propylene, and the catalyst.

11. The method according to claim 6, wherein the polyolefin has stereoregularity (XI) of 90% or higher, and
wherein the stereoregularity (XI) is measured by the weight percent of the insoluble fraction of the polyolefin polymer, after adding the polyolefin polymer into a boiled ortho-xylene and heating it for 1 hr to reflux the ortho-xylen.

12. A method for preparing a polyolefin comprising polymerizing at least one olefin monomer in the presence of the catalyst according to claim 5.

13. The method according to claim 12, wherein the polymerization is carried out at a temperature of 25 to 500° C. under a pressure of 1 to 100 kgf/cm² for 1 to 24 hr.

14. The method according to claim 12, wherein the olefin monomers are selected from the group consisting of ethylene, propylene, 1-butene, 1-pentene, 1-hexene, 4-methyl-1-pentene, 1-octene, 1-decene, 1-dodecene, 1-tetradecene, 1-hexadecene, 1-octadecene, 1-eicosene, and a combination thereof.

15. The method according to claim 12, wherein the activity of the catalyst is 20 kg/mmol·hr or more, as calculated by the ratio of weight (kg) of the produced polymer per mmol of the used catalyst per unit time (hr), after propylene polymerization is carried out at a temperature of 25 to 500° C. under a pressure of 1 to 100 kgf/cm² for 1 to 24 hr by using triethylaluminum, hydrogen, propylene, and the catalyst.

16. The method according to claim 12, wherein the activity of the catalyst is 1.0 kg/gCat·hr or more, as calculated by the ratio of the weight (kg) of the produced polymer per weight (g) of the used catalyst per unit time (hr), after propylene polymerization is carried out at a temperature of 25 to 500° C. under a pressure of 1 to 100 kgf/cm² for 1 to 24 hr by using triethylaluminum, hydrogen, propylene, and the catalyst.

17. The method according to claim 12, wherein the polyolefin has stereoregularity (XI) of 90% or higher, and
wherein the stereoregularity (XI) is measured by the weight percent of the insoluble fraction of the polyolefin polymer, after adding the polyolefin polymer into a boiled ortho-xylene and heating it for 1 hr to reflux the ortho-xylene.

* * * * *